United States Patent
Schotten et al.

(10) Patent No.: US 9,138,159 B2
(45) Date of Patent: Sep. 22, 2015

(54) NON-INVASIVE CLASSIFICATION OF ATRIAL FIBRILLATION BY PROBABILISTIC INTERVAL ANALYSIS OF A TRANSESOPHAGEAL ELECTROCARDIOGRAM

(75) Inventors: Ulrich Schotten, AAchen (DE); Stef Zeemering, Maastricht (NL); Bart Maesen, Riemst (BE)

(73) Assignee: Maastricht University, Maastricht (NL)

( * ) Notice: Subject to any disclaimer, the term of this patent is extended or adjusted under 35 U.S.C. 154(b) by 3 days.

(21) Appl. No.: 14/119,361

(22) PCT Filed: May 22, 2012

(86) PCT No.: PCT/EP2012/059509
§ 371 (c)(1),
(2), (4) Date: Mar. 14, 2014

(87) PCT Pub. No.: WO2012/160066
PCT Pub. Date: Nov. 29, 2012

(65) Prior Publication Data
US 2015/0038863 A1    Feb. 5, 2015

(30) Foreign Application Priority Data

May 23, 2011  (EP) .................................... 11167091

(51) Int. Cl.
| A61B 5/046 | (2006.01) |
| A61B 5/0452 | (2006.01) |
| A61B 5/04 | (2006.01) |
| A61B 5/00 | (2006.01) |
| A61N 1/362 | (2006.01) |

(52) U.S. Cl.
CPC .............. *A61B 5/046* (2013.01); *A61B 5/04012* (2013.01); *A61B 5/04525* (2013.01); *A61B 5/7275* (2013.01); *A61N 1/3624* (2013.01)

(58) Field of Classification Search
None
See application file for complete search history.

(56) References Cited

U.S. PATENT DOCUMENTS

| 5,755,736 A * | 5/1998 | Gillberg et al. .................. 607/4 |
| 2004/0249420 A1 * | 12/2004 | Olson et al. ..................... 607/9 |
| 2010/0004550 A1 | 1/2010 | Ishay et al. |
| 2010/0056940 A1 * | 3/2010 | Moorman et al. ............ 600/518 |
| 2013/0079654 A1 * | 3/2013 | Patel et al. .................... 600/518 |
| 2013/0096449 A1 * | 4/2013 | Patel et al. .................... 600/516 |

OTHER PUBLICATIONS

International Search Report and Written Opinion of PCT/EP2012/059509, filed May 22, 2012.

(Continued)

*Primary Examiner* — Kennedy Schaetzle
(74) *Attorney, Agent, or Firm* — Steven M. Koehler; Westman, Champlin & Koehler, P.A.

(57) ABSTRACT

The invention relates to a computer-implemented method for determining an AF complexity value. The method includes applying a template matching algorithm to an ECG signal to obtain a set of candidate deflections and identifying intrinsic deflections within the set of candidate deflections. The method further includes determining a number of intrinsic deflections and a number of far-field deflections within the set of candidate deflections, based on the identified intrinsic deflections, and determining the AF complexity value as a ratio between the number of far-field deflections and the number of intrinsic deflections.

20 Claims, 11 Drawing Sheets

(56) References Cited

OTHER PUBLICATIONS

Takahashi et al: "Characterization of Electrograms Associated With Termination of Chronic Atrial Fibrillation by Catheter Ablation", Journal of the American College of Cardiology, Elsevier, New York, NY, US, vol. 51, No. 10, Mar. 4, 2008, pp. 1003-1010.

R.J. Hunter et al: "Validation of a classification system to grade fractionation in atrial fibrillation and correlation with automated detection systems", EUROPACE, vol. 11, No. 12, Dec. 1, 2009, pp. 1587-1596.

Jason NG et al: "Measuring the Complexity of Atrial Fibrillation Electrograms", Journal of Cardiovascular Electrophysiology, vol. 21, No. 6, Jun. 1, 2010.

P. S. Cuculich et al: "Noninvasive Characterization of Epicardial Activation in Humans With Diverse Atrial Fibrillation Patterns", Circulation, vol. 122, No. 14, Oct. 5, 2010, pp. 1364-1372.

Nademanee Koonlawee et al: "A new approach for catheter ablation of atrial fibrillation: mapping of the electrophysiologic substrate", Journal of the American College of Cardiology, Elsevier, New York, NY, US, vol. 43, No. 11, Jun. 2, 2004, pp. 2044-2053.

\* cited by examiner

| Patient | $N_D$ | $N_I$ | AF complexity |
|---|---|---|---|
| A | 647 | 500 | 0.29 |
| B | 2215 | 641 | 2.46 |

FIG. 11

NON-INVASIVE CLASSIFICATION OF ATRIAL FIBRILLATION BY PROBABILISTIC INTERVAL ANALYSIS OF A TRANSESOPHAGEAL ELECTROCARDIOGRAM

CROSS-REFERENCE TO RELATED APPLICATION

The present application is a national stage filing of International patent application Serial No. PCT/EP2012/059509, filed May 22, 2012, and published as WO 2012/160066 A1 in English.

FIELD OF THE INVENTION

The discussion below is merely provided for general background information and is not intended to be used as an aid in determining the scope of the claimed subject matter.

Generally, aspects of the invention relates to the field of cardiovascular diseases. More specifically, the invention relates to the field of classification of atrial fibrillation based on an analysis of electrocardiograms.

BACKGROUND

In modern medicine, the choice for therapeutic approaches often depends on the stage of the disease process. This principle holds true in the majority diseases like cancer, neurological and psychiatric disorders, many infections but also applies for cardiovascular and metabolic diseases such as heart failure, peripheral artery disease, diabetes, hypertension and angina pectoris. Stage-specific therapy has largely contributed to the strong increase in life expectancy in our society and more specifically to the reduction of mortality of cardiovascular diseases.

In atrial fibrillation (AF), a classification of the disease does not exist yet which is due to the fact that the main electrophysiological alterations which determine the stability of AF have only been identified very recently. Two electrophysiological techniques that are currently used for the quantification of the complexity of the substrate of AF include time frequency analysis of surface electrocardiograms (ECGs) and ECG imaging. The first technique uses Fast-Fourier or principle component analysis of the atrial surface ECG signal and can adequately estimate the complexity of AF in the right but not in the left atrium. Because the complexity of the AF substrate is larger in the posterior wall of the left atrium compared to the right atrial free wall and because the left atrium is more important for the stability of AF, this technique is not likely to provide an adequate classification of AF or a good estimation of the success of AF therapy. The second technique has been developed to reconstruct the epicardial electrical activity in atria and ventricles from body surface potential maps and the individual anatomy of the thorax. In order to implement this technique, an ECG-triggered CT or MRI of the thorax including localization of the electrodes is required, which are expensive, time-consuming and, in case of CT, afflicted with radiation exposure.

Consequently, current therapeutic regimens are most often chosen based on clinical symptoms and the duration of AF (paroxysmal or persistent AF). Although helpful, these categories do not necessarily reflect the quality and the degree of electrophysiological changes resulting in AF. For example, in patients with persistent AF the relative contribution of abnormal impulse formation or the severity of the electrophysiological substrate are usually unknown and not taken into account during the therapeutic decision-making process. Yet it appears likely that the nature of the electrophysiological changes resulting in AF strongly affects the efficacy of a therapeutic intervention emphasizing the need for a classification of AF.

The main advantage of the classification of AF would be the possibility to implement a "graded therapy" of AF. A "graded therapy" is a therapy that depends on the kind and the degree of the electrophysiological alterations in a specific patient. A large variety of therapeutic options exist in AF patients: pharmacological cardioversion, electrical cardioversion, pulmonary vein isolation, extended ablation therapies, rate control, anticoagulant therapy, and organ-protective upstream therapy. The challenge is to choose the right therapy for the right patient. In order to define the best choice in an individual patient, the kind and degree of pathophysiological changes in the atrium needs to be determined which means to classify the arrhythmia in each individual patient. Furthermore, such a classification will allow basic researchers and clinicians to better understand the mode of action of anti-arrhythmic drugs and to evaluate new anti-arrhythmic working mechanisms, to develop individualized therapy with anti-arrhythmic drugs, and to optimize ablation therapies in terms of patient selection, ablation technique (RF, ultrasound, cryo), and selection of ablation sites.

As the foregoing illustrates, there is a need to provide means for classifying AF in a manner that eliminates at least some of the drawbacks described above.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background. One aspect of the invention discloses a computer-implemented method for determining an AF complexity value. The method includes applying a template matching algorithm to an ECG signal to obtain a set of candidate deflections and identifying intrinsic deflections within the set of candidate deflections. The method further includes determining a number of intrinsic deflections and a number of far-field deflections within the set of candidate deflections, based on the identified intrinsic deflections, and determining the AF complexity value as a ratio between the number of far-field deflections and the number of intrinsic deflections.

An aspect of the invention is based on the recognition that determination of the AF complexity value as a ratio between the number of far-field deflections and the number of intrinsic deflections enables classification of AF in a non-invasive manner that does not require thorax MRI or thorax CT as some prior art approaches described above.

In one embodiment, the step of determining the number of intrinsic deflections and the number of far-field deflections may comprise determining the number of intrinsic deflections as the number of identified intrinsic deflections, and determining the number of far-field deflections as the difference between the total number of deflections within the set of candidate deflections and the number of identified intrinsic deflections.

In an alternative embodiment, the step of determining the number of intrinsic deflections and the number of far-field deflections may comprise determining probability distribution of an intrinsic deflection interval based on the identified intrinsic deflections, assigning each deflection in the set of candidate deflections either to a set of intrinsic deflections or a set of far-field deflections based on the probability distribution of the intrinsic deflection interval, determining the number of intrinsic deflections as the number of deflections within the set of intrinsic deflections, and determining the number of far-field deflections as the number of deflections within the set of far-field deflections.

In such an embodiment, each deflection in the set of candidate deflections may be assigned either to the set of intrinsic deflections or the set of far-field deflections in a manner that maximizes the intrinsic deflection interval likelihood. The step of assigning each deflection in the set of candidate deflections either to the set of intrinsic deflections or the set of far-field deflections may be performed using a greedy algorithm.

In various embodiments, the intrinsic deflections may be identified based on a maximum interval threshold, an order of deflection features, and a threshold for each of the deflection features. These criteria may be either pre-determined and/or stored in the memory of the computing device implementing the method or provided to the computing device by the user.

In an embodiment, the deflection features may include one or more of a correlation coefficient of a deflection, an amplitude of the deflection, a duration of the deflection, and a slope of the deflection.

In one embodiment, the threshold for each of the deflection features could comprise a fixed threshold. This could be advantageous in a situation where one has prior knowledge about the threshold value for a deflection feature. Alternatively, the threshold for each of the deflection features could comprise a dynamic threshold and the intrinsic deflections may be identified further based on a percentage of intervals that are allowed to exceed the maximum interval threshold. This could be advantageous in a situation where one has no prior knowledge about the threshold value for a deflection feature. A suitable threshold is determined automatically.

In an embodiment, the method may further include the step of classifying the AF based on the determined AF complexity value, providing a relatively easy and non-invasive classification of AF.

In an embodiment, the method may further include selecting a treatment from a set of treatments based on the determined AF complexity value, thereby enabling graded therapy.

In an embodiment, the method may further include determining AF cycle length (AFCL) based on the identified intrinsic deflections, which could be useful for determining the likelihood for cardioversion at the moment of the measurement.

In various embodiments of the above-described method, the ECG signal comprises a trans-esophageal ECG signal, advantageously allowing analysis of the substrate of AF in the posterior wall of the left atrium.

In another aspect of the invention, an ECG device comprising means configured for carrying out steps of the method is proposed. Such an ECG device may further be configured to display of the determined AF complexity value, the determined classification of AF and/or the assigned treatment.

Still other aspects of the invention relate to a, preferably non-transitory, computer program for carrying out steps of one or more of the methods described above.

Hereinafter, embodiments of the invention will be described in further detail. It should be appreciated, however, that these embodiments may not be construed as limiting the scope of protection for the present invention.

DETAILED DESCRIPTION OF THE ILLUSTRATIVE EMBODIMENTS

Figure 1:
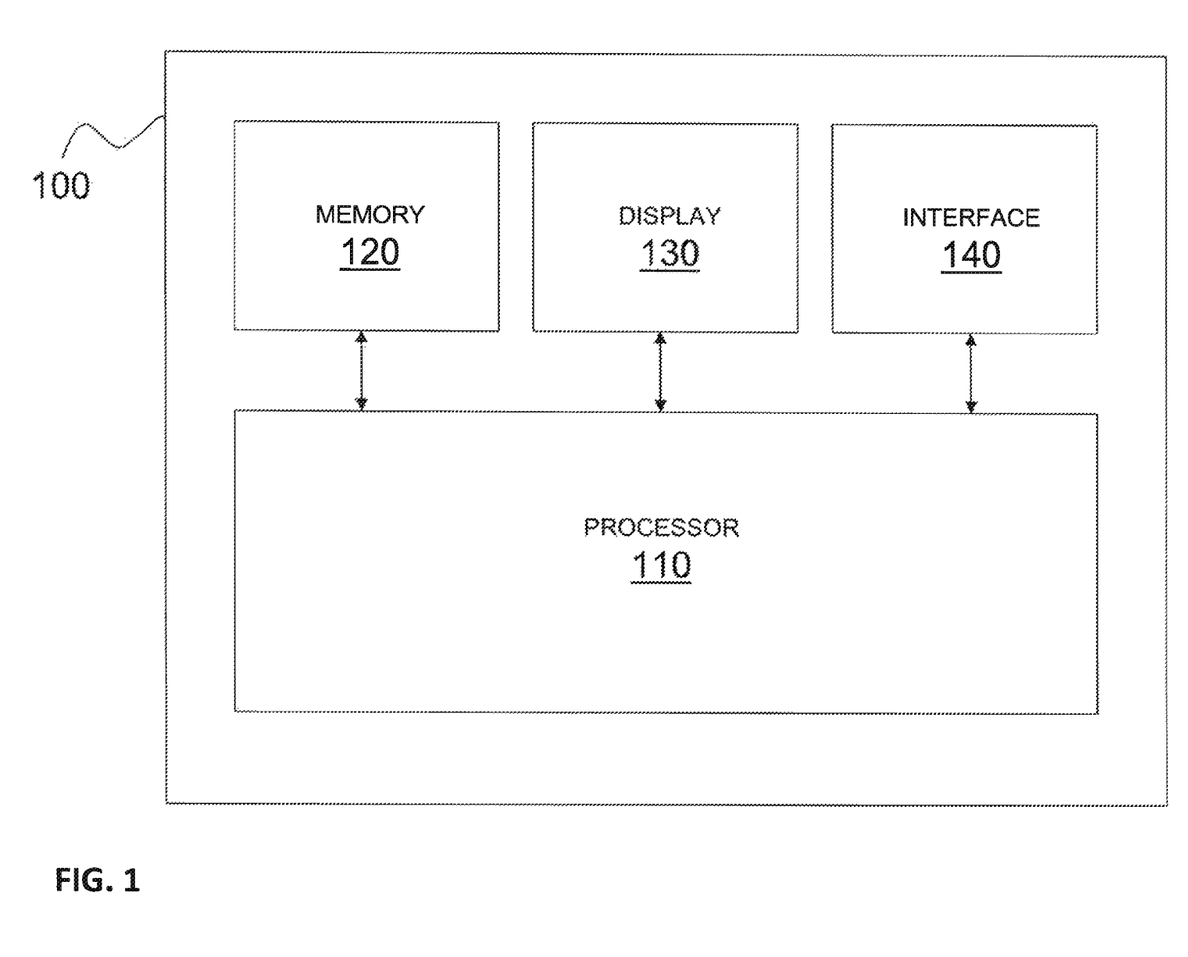
FIG. 1 provides a schematic illustration of a system 100 operable to implement one or more aspects of the present invention.

FIG. 1 provides a schematic illustration of a system 100 operable to implement one or more aspects of the present invention. As shown, the system 100 includes a processor 110, a memory 120, and a display 130, connected to the processor 110. The processor 110 is configured to perform some of the steps for classifying AF, as described below. The memory 120 may be operable to store instructions that, when executed by the processor 110, perform any of the methods described herein. The display 130 is configured to display the results of the method steps performed by the processor 110. The system 100 may further optionally include an interface 140 configured to receive user input from one or more user input devices (e.g., keyboard, mouse, not shown in FIG. 1) and forward the user input to processor 110.

Connections between different components in FIG. 1 may use different protocols as is known in the art. It will be appreciated that the system shown herein is illustrative and that variations and modifications are possible. In an embodiment, the system 100 may be included in an ECG device.

Figure 2:
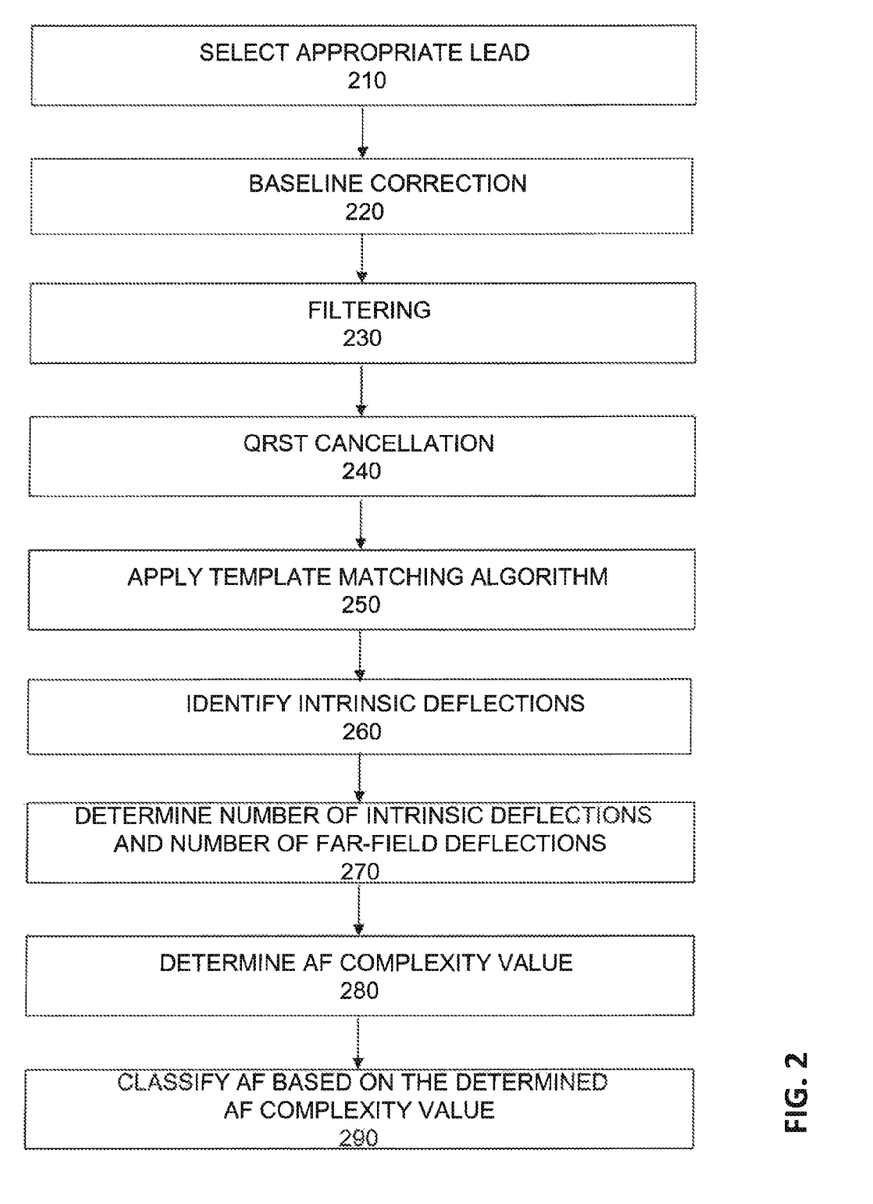
FIG. 2 provides a flow diagram of method steps for classifying AF, according to one embodiment of the present invention.

FIG. 2 provides a flow diagram of method steps for classifying AF, according to one embodiment of the present invention. While the method steps are described in conjunction with FIG. 1, persons skilled in the art will recognize that any system configured to perform the method steps, in any order, is within the scope of the present invention.

Figure 3:
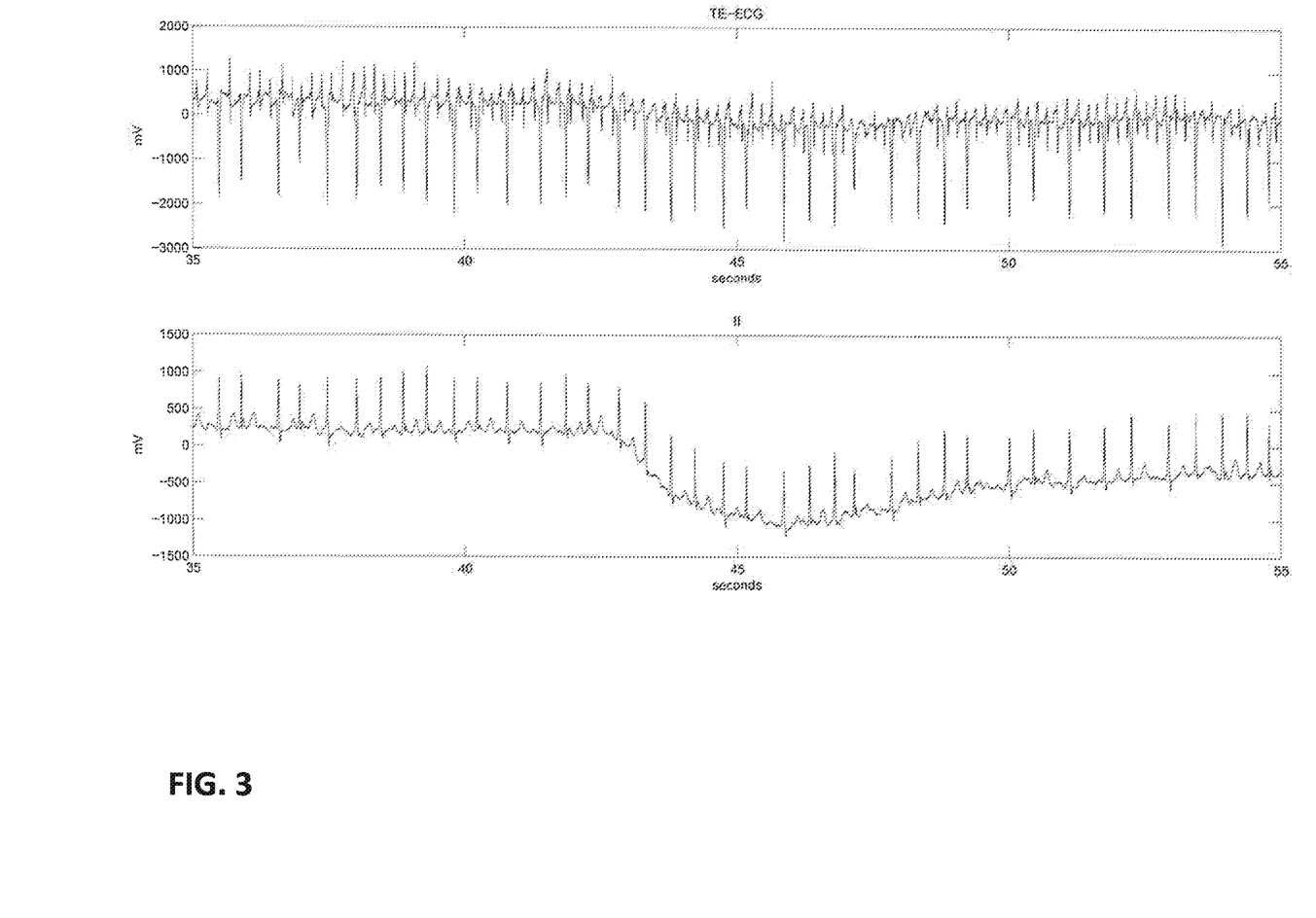
FIG. 3 illustrates original TE-ECG lead and limb lead II signals.

The method is carried out based on an ECG signal data, preferably trans-esophageal (TE) ECG data. To that end, 2 to 4 unipolar electrograms (Wilson central terminal serves as reference) may be recorded with either stiff catheters which can be protruded through mouth or nose of a patient or with a swallowable electrode. The recorded electrograms may be included in a file containing a multi-lead ECG signal. Persons skilled in the art will recognize that while data recorded using only one electrode would also be sufficient for carrying out the method described below, using at least two electrodes allows better localizing electrode's position in the esophagus, based on A/V ratio. Thus, the file would preferably contain at least one trans-esophageal electrogram and the right arm (RA), left arm (LA) and left leg (LL) lead recordings. FIG. 3 illustrates an original (i.e., "as recorded") TE-ECG lead signal (the upper graph) and an original limb lead II signal (the lower graph).

The method begins in a step 210, where, based on the TE-ECG data available, the user may select for further analysis, via the user interface 140, a signal recorded via the most appropriate TE-ECG lead. In a preferred embodiment, the most appropriate lead would record the TE-ECG signal that shows the largest amplitude of the atrial deflections. Such a signal would have the highest A/V ratio or would have a clear A signal and a negative V signal (above the ventricle).

In step 220, the processor 110 may perform baseline correction of the selected signal in order to remove baseline wander of the selected signal, due to for instance respiration and body movement.

Figure 4:
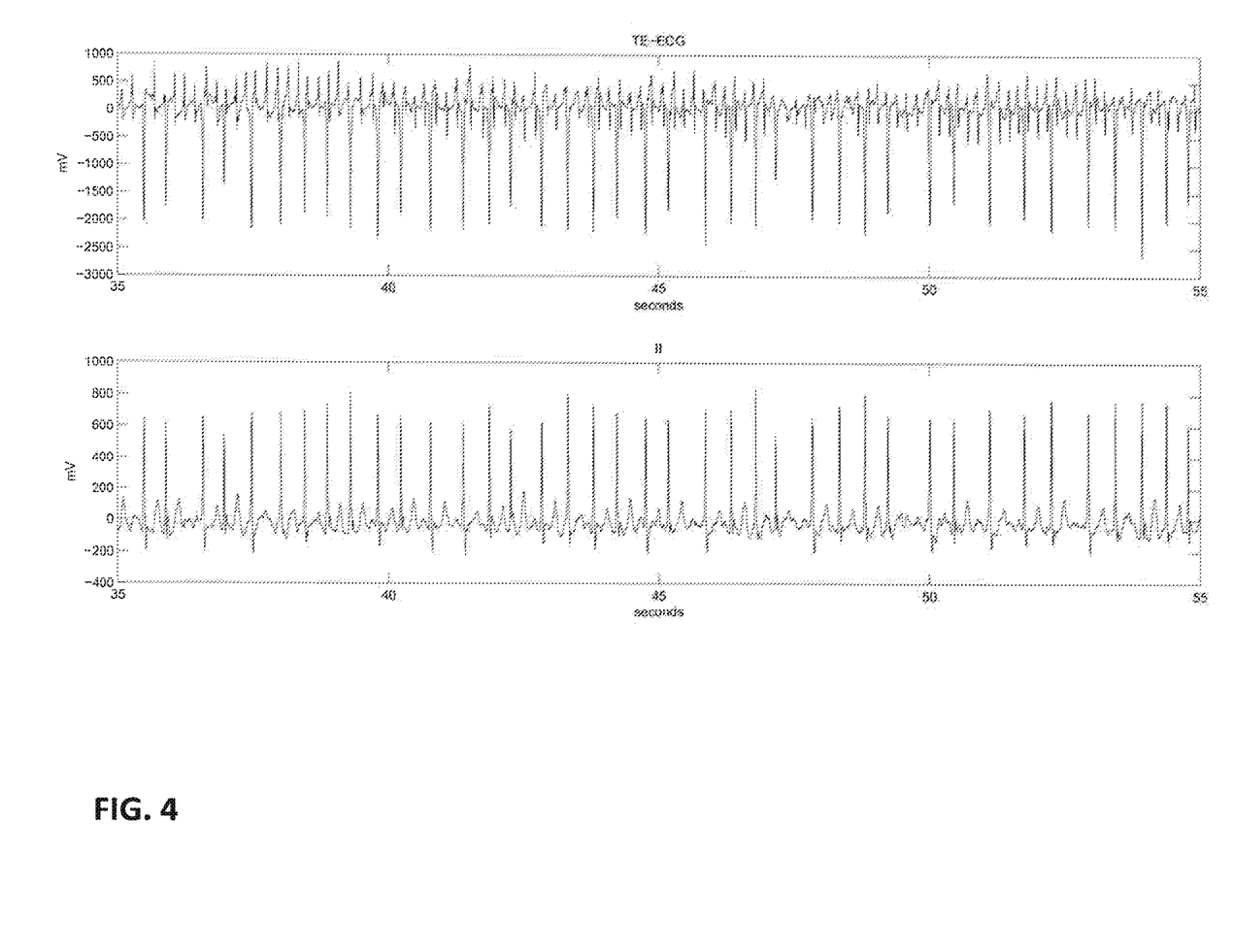
FIG. 4 illustrates baseline corrected and filtered TE-ECG and limb lead II signals.

In step 230, the processor 110 may filter the signal with corrected baseline using a high-pass and low-pass finite impulse response (FIR) filter, possibly at user-specified frequencies (typically 0.5 to 100 Hz), in a manner known in the art. If a periodogram of the signal indicates the presence of power line interference, an infinite impulse response (IIR) notch filter may be applied at the corresponding frequency (typically 50 Hz or 60 Hz) in order to exclude common 50 or 60 Hz AC noise sources typically present in clinical environments, where recordings of ECG data are normally performed. FIG. 4 illustrates a baseline corrected and filtered (0.5-100 Hz) TE-ECG signal (the upper graph) and a baseline corrected and filtered (0.5-100 Hz) limb lead II signal (the lower graph).

Figure 5:
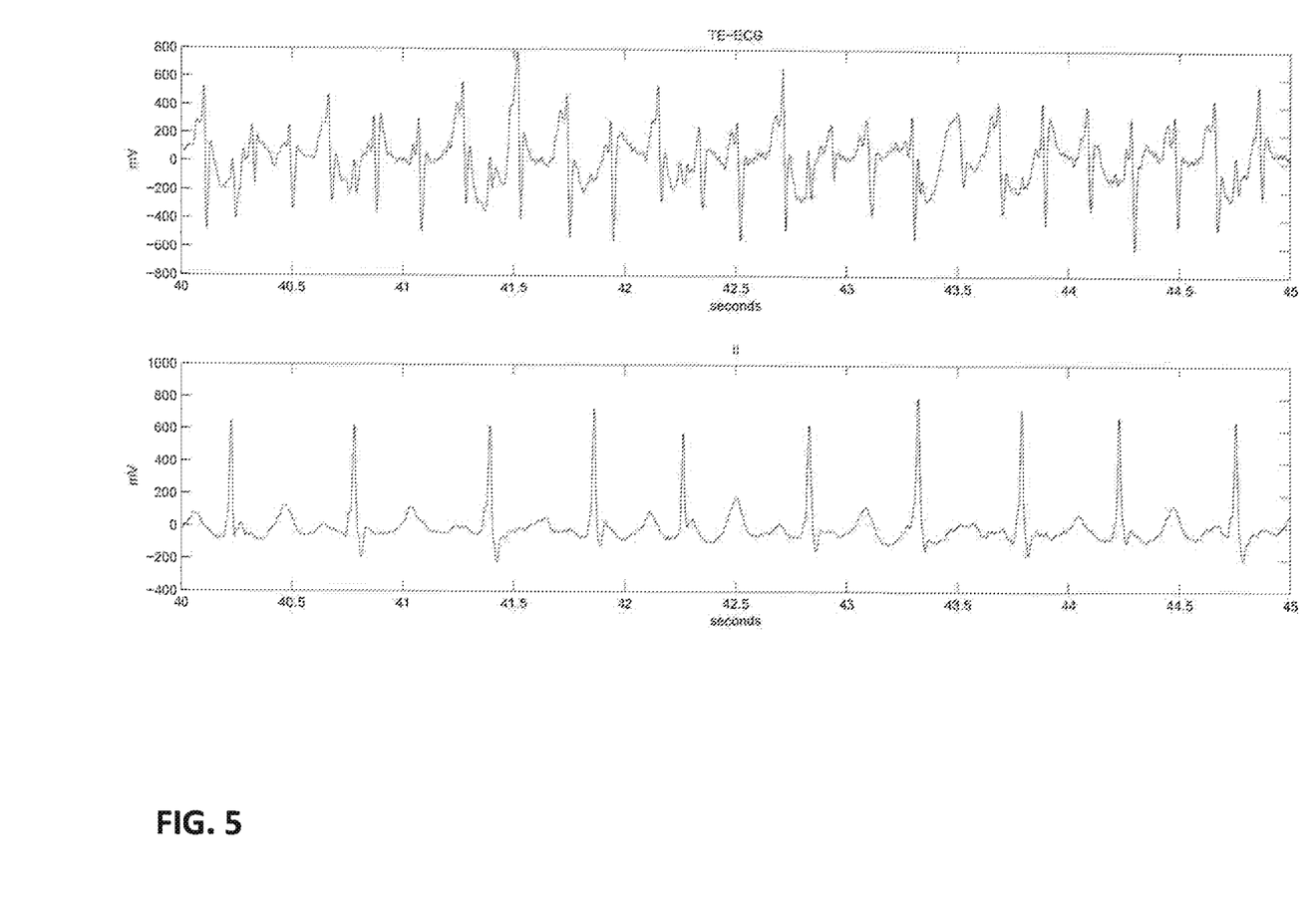
FIG. 5 illustrates a TE-ECG signal after QRST cancellation and a limb lead II signal without QRST cancellation.

In step 240, the processor 110 may detect the ventricular QRST complex using the Pan-Tompkins R-peak detection algorithm and eliminate from the signal by a QRST cancellation algorithm, in a manner known in the art. The QRST cancellation may be done to avoid detection of ventricular activations as atrial electrical activity. An example of a TE-ECG signal after QRST cancellation is depicted in the upper graph of FIG. 5. In the lower graph of FIG. 5 the corresponding limb lead II without QRST cancellation is depicted.

Steps 210-240 are optional as they relate to well-known means for data import and selection and pre-processing of signals. Steps 250-290 described below could also be implemented using a single ECG signal as it was originally recorded (i.e., without undergoing baseline correction, filtering, and QRST cancellation).

Figure 6:
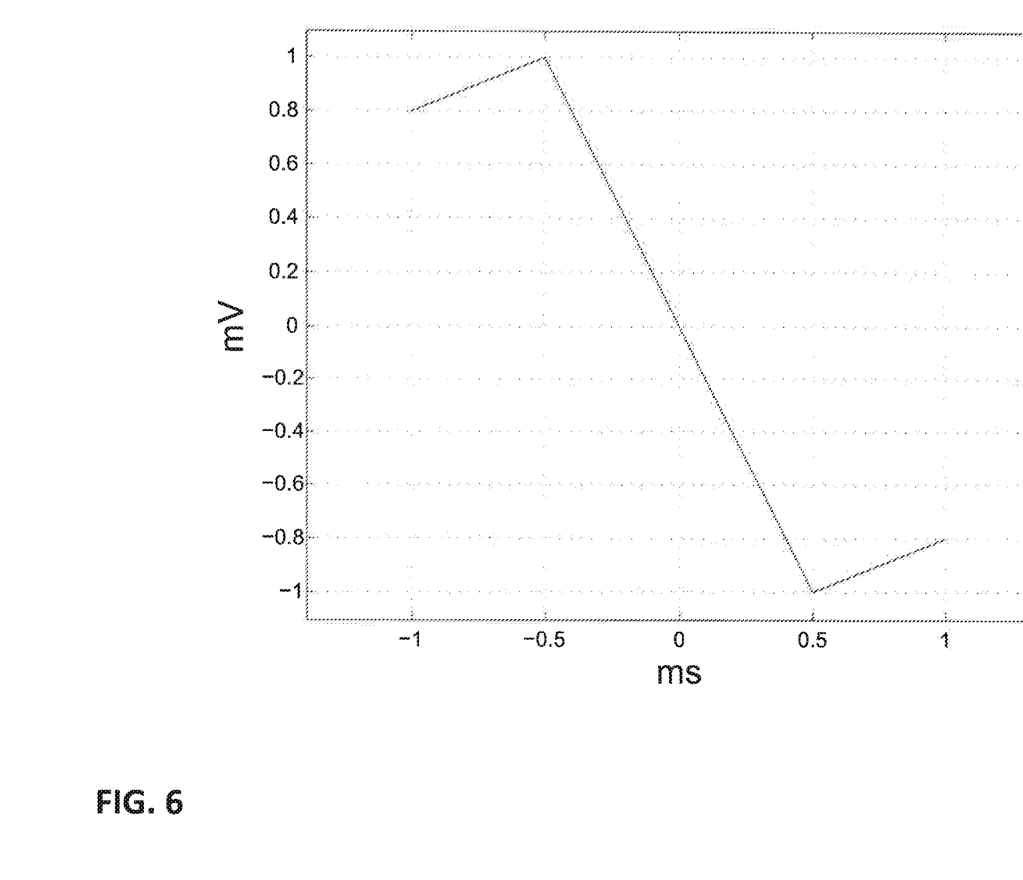
FIG. 6 illustrates an exemplary deflection template.

In step 250, using one or more deflection templates, the processor 110 applies a sensitive template matching algorithm to the QRST-cancelled ECG signal. To that end, the processor may use default templates and/or user-defined templates. An exemplary template according to one embodiment of the present invention is illustrated in FIG. 6 depicting a single deflection consisting of a first ascending limb, followed by a down stroke and a second ascending limb. In other embodiments, templates can have different morphologies and different durations. The user may define templates using the user interface 140. The templates may be stored in the memory 120.

Figure 7:
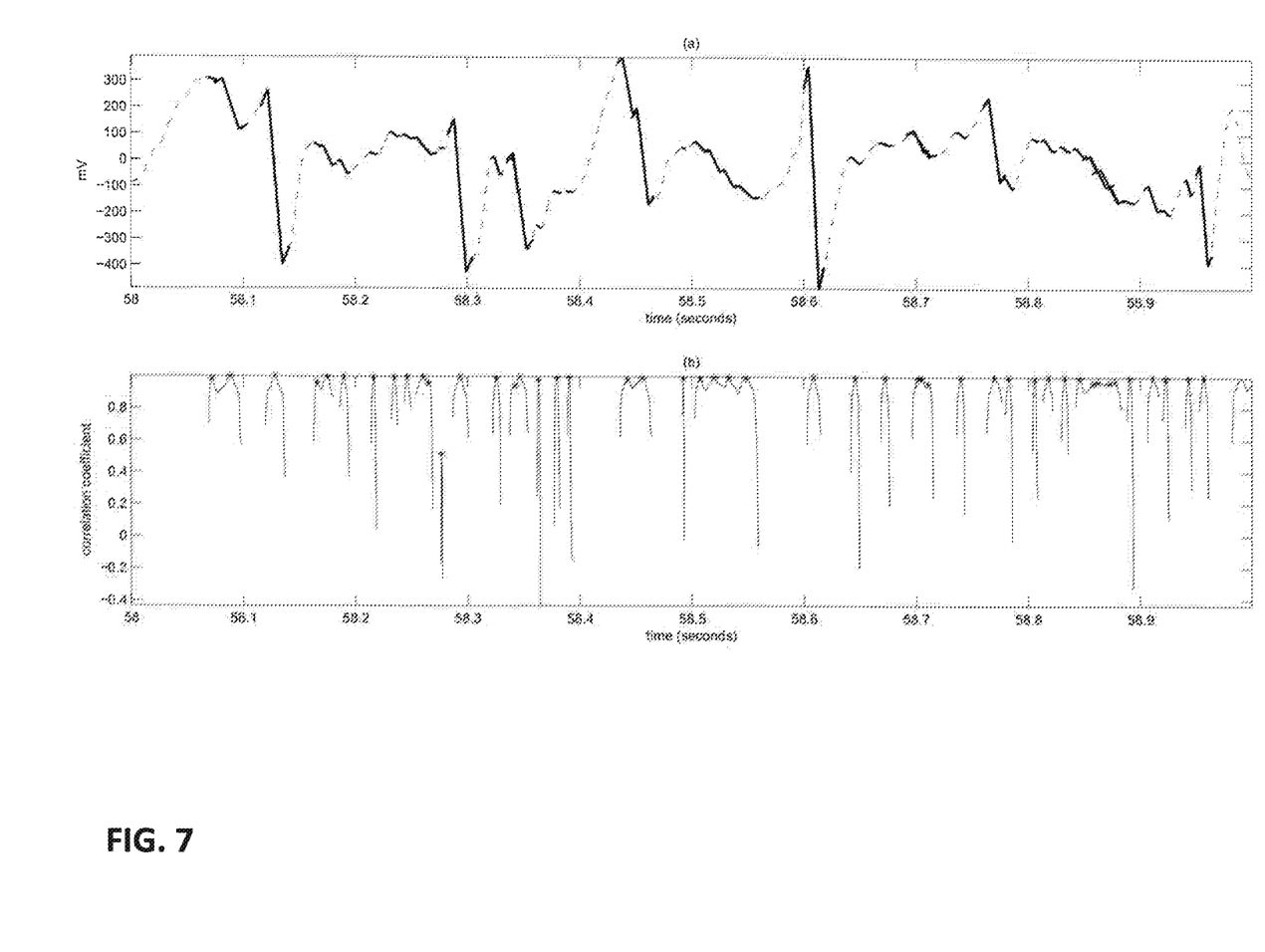
FIG. 7 illustrates, in a portion of the QRST-cancelled TE-ECG signal, deflections detected by applying the template matching algorithm and a corresponding correlation plot.

FIG. 7 illustrates, in a part of the QRST-cancelled TE-ECG signal, deflections detected by applying the template matching algorithm (the upper graph) and a corresponding correlation plot showing local maxima (the lower graph). The correlation plot indicates the correlation coefficients of the best scoring template (in terms of morphology and duration) for each moment in time. Given a signal s, a set of template morphologies M and a set of template durations D, the correlation coefficient C at time instant k is computed as $$C(k)=\max_{m,d}\{r_{m,d}(k)|m\in M, d\in D\},$$

where $r_{m,d}(k)$ denotes the sample correlation coefficient of the template with morphology m (m∈M) and duration d (d∈D) and the signal s centred at s(k).

All local maxima in the correlation plot may be detected using the difference operator. The local maxima, and corresponding template morphologies and durations, may then be marked as potential deflection sites. As a result, the sensitive template matching procedure provides a set of candidate deflections.

Figure 8:
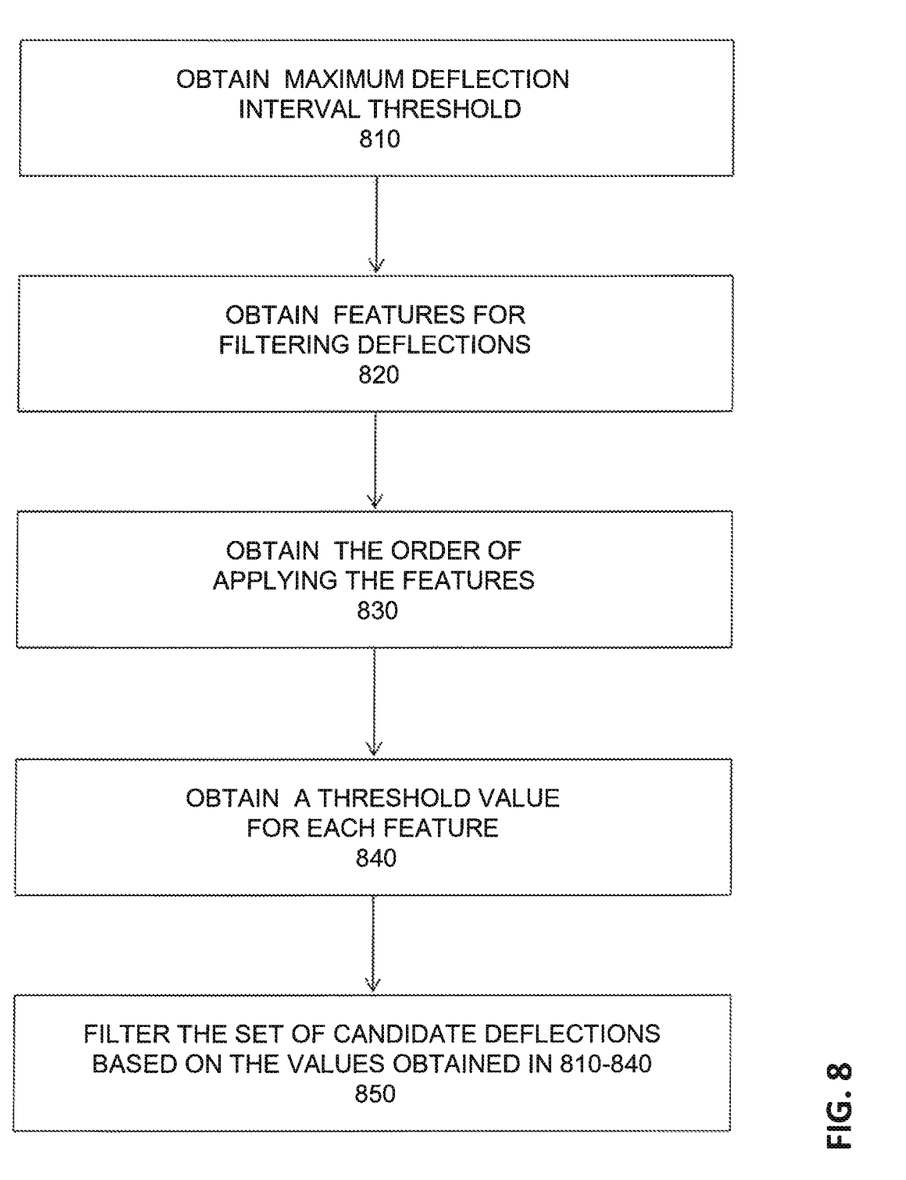
FIG. 8 provides a flow diagram of method steps for identifying strong intrinsic deflections from the set of candidate deflections, according to one embodiment of the present invention.

Of the candidate deflections, in step 260, the processor 110 selects a subset of deflections by implementing the filtering procedure illustrated in FIG. 8. The goal of the procedure illustrated in FIG. 8 is to retain only strong intrinsic deflections.

FIG. 8 provides a flow diagram of method steps for identifying strong intrinsic deflections from the set of candidate deflections, according to one embodiment of the present invention. Similar to the method steps illustrated in FIG. 2, while the method steps of FIG. 8 are described in conjunction with FIG. 1, persons skilled in the art will recognize that any system configured to perform the method steps, in any order, is within the scope of the present invention.

The filtering procedure begins in step 810 where the processor 110 obtains a value of the maximum deflection interval threshold. Such a value may be e.g. pre-determined and stored in the memory 120, where the processor 110 obtains the value stored in the memory 120. Alternatively, such a value may be provided by the user, via the user interface 140. The value of the maximum deflection interval threshold may be based e.g. on electrophysiological knowledge of the normal range of AFCL in AF patients and/or based on visual inspection of the signal after the template-matching procedure.

In step 820, the processor 110 obtains information regarding features that are to be used to filter the deflections. Possible features include a correlation coefficient associated with a deflection, an amplitude of a deflection, a duration of a deflection, and/or a slope of a deflection. Similar to the information obtained in step 810, this information may either be pre-determined and provided to the processor from the memory 120 or provided by the user via the user interface 140.

In step 830, the processor 110 obtains information regarding the order in which the selected features are to be applied.

In step 840, for each deflection feature, the processor 110 obtains information indicating either a fixed threshold or a dynamic threshold. A fixed threshold means that if a deflection fails to meet this threshold, the deflection is removed. A dynamic threshold means that the value of the threshold is optimized to remove as many deflections as possible, without creating a predefined percentage of deflection intervals that exceed the maximum deflection interval threshold.

Again, the information provided to the processor 110 in steps 830 and 840 may either be pre-determined and provided to the processor from the memory 120 or provided by the user via the user interface 140.

In step 850, the processor 110 filters the set of candidate deflections according to the filtering parameters obtained in steps 810-840. The deflections that remain after the filtering procedure are assumed to be a subset of the true intrinsic deflections.

In one exemplary embodiment, steps 810-850 could be implemented as follows. For example, the user sets the maximum interval threshold to 250 milliseconds (ms). Then the user selects correlation coefficients and amplitudes of deflections as features. The user specifies that the correlation coefficient should be applied first and then the amplitude should be applied. The user chooses a fixed threshold having a value of 0.5 for the correlation coefficient and a dynamic threshold for the amplitude. The user also specifies that a maximum of 5% of the created deflection intervals may exceed the maximum deflection interval threshold. The filtering procedure carried out by the processor 110 will then removes all candidate deflections with a correlation coefficient less than 0.5. Next, the remaining deflections are filtered according to the dynamic threshold for amplitude. This means that the filtering procedure increases the amplitude threshold, thereby removing deflections until at most 5% of all remaining deflection intervals exceed the maximum deflection interval threshold.

Figure 9:
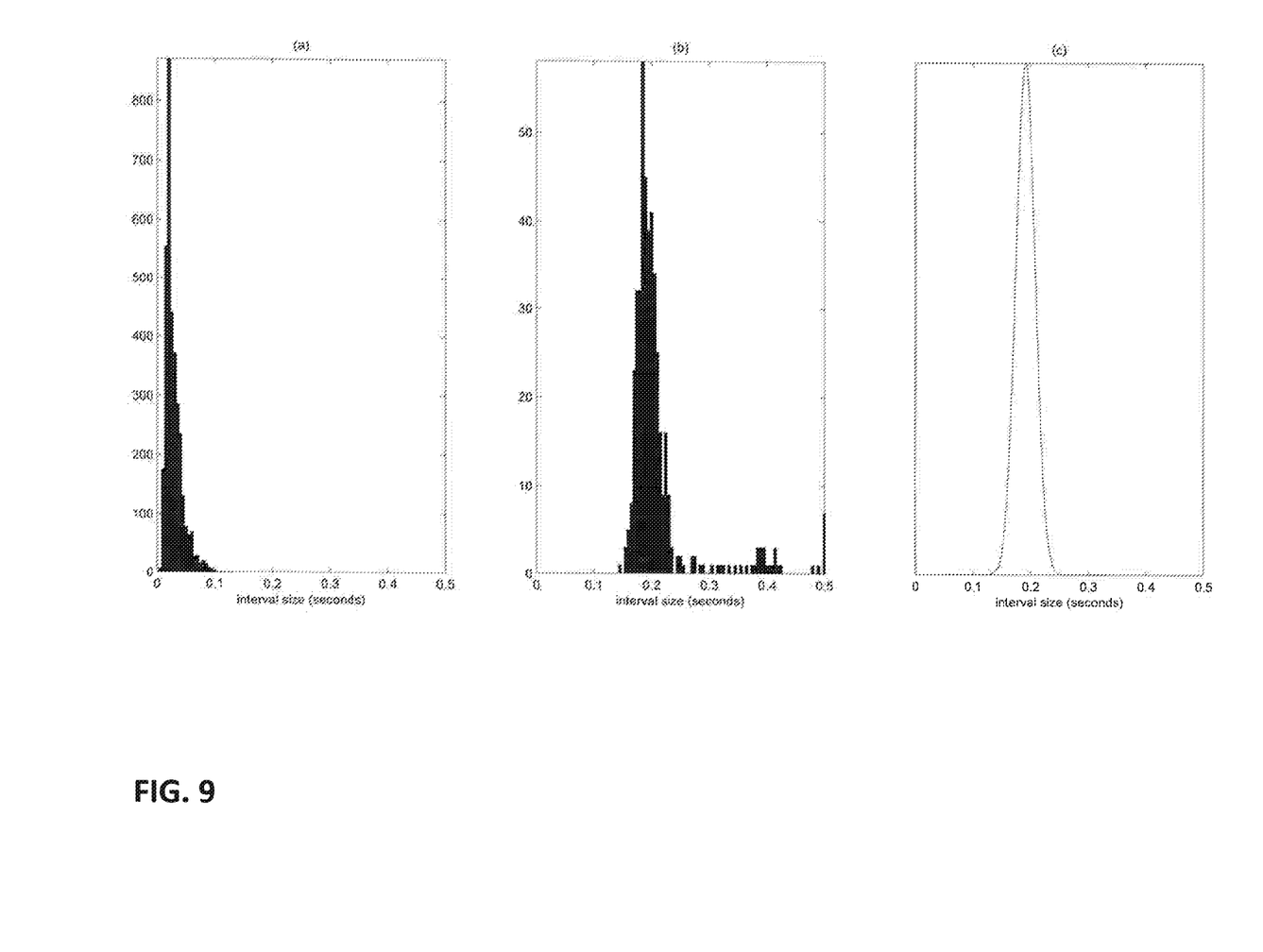
FIG. 9(a) illustrates an exemplary histogram of deflection intervals created by the deflections resulting from the sensitive template matching procedure.
FIG. 9(b) illustrates an exemplary histogram of deflection intervals where the deflections have been filtered to retain only strong intrinsic deflections.
FIG. 9(c) illustrates a Gaussian deflection interval distribution function fitted to the strong intrinsic deflections illustrated in FIG. 9(b).

After the filtering procedure of FIG. 8, the processor 110 is able to estimate the interval distribution of the true intrinsic deflections from the interval distribution of the subset by fitting probability density function to the distribution of the time intervals between the identified strong intrinsic deflections. This is illustrated in FIG. 9 providing graphs (a), (b), and (c). The graph (a) depicts a histogram of deflection intervals created by the deflections resulting from the sensitive template matching procedure of step 250, described above (i.e., intervals created by the candidate deflections). The graph (b) depicts a histogram of deflection intervals where the deflections have been filtered according to the filtering procedure described in FIG. 8 with maximum interval threshold of 250 ms and a dynamic threshold for amplitude and an associated long interval percentage of 5%. The graph (c) depicts a Gaussian deflection interval distribution function fitted to the strong intrinsic deflections identified by the filtering procedure of FIG. 8. The fitted Gaussian function such as the one illustrated in graph (c) allows e.g. estimating the value of the AFCL (as the interval corresponding to the peak of the Gaussian function) and/or assessing the viability of the substrate of AF based on the standard deviation of the Gaussian function. For the Gaussian function illustrated in FIG. 9(c), the AFCL can be estimated to be 0.2 seconds.

In step 270, the processor 110 uses the interval distribution of the strong intrinsic deflections to compute the expected total number of true intrinsic deflections $N_I$ and the number of far-field deflections $N_F$ that are present during the time course of the measurement. The number of true intrinsic deflections $N_I$ can be obtained by estimating the number of expected intrinsic deflections given the duration of the signal and the expected deflection interval determined from the interval distribution of the true intrinsic deflections. The number of far-field deflections $N_F$ can be determined as the difference between the number of candidate deflections $N_D$ and the number of true intrinsic deflections.

For some applications, a set of candidate deflections identified as a result of the template-matching procedure of step 250 is adequate for estimating the number of candidate deflections $N_D$.

However, the set identified as a result of performing step 250 may include false positives, i.e. may identify certain features as "candidate deflections" even though those features are, in reality, just artifacts due to e.g. noise or other disturbances. Therefore, in an optional embodiment, the set obtained as a result of performing step 250 could be filtered further to remove deflections attributed to disturbances, yielding a smaller set of deflections which could then be used as a set of candidate deflections for determining the number of candidate deflections $N_D$. To that end, a filtering procedure similar to that described in FIG. 8 could be applied to the result of the template-matching of step 250. For example, the user may set the maximum interval threshold to 250 ms. Then the user may select correlation coefficients and amplitudes of deflections as features and specify that the correlation coefficient should be applied as a correlation feature before applying the amplitude. The user may then choose a fixed threshold having a value of 0.5 for the correlation coefficient and a dynamic threshold for the amplitude. The user may also specify that none (0%) of the created deflection intervals may exceed the maximum deflection interval threshold. The filtering procedure carried out by the processor 110 will then remove all deflections with a correlation coefficient less than 0.5. Next, the remaining deflections could be filtered according to the dynamic threshold for amplitude. A result of such filtering is illustrated in FIG. 10(a). The aim of this exemplar intermediate filtering step is to estimate the smallest amplitude of an intrinsic deflection and use this value as an amplitude threshold that separates artifacts from true candidate deflections. Optionally, step 260 of identifying strong intrinsic deflections could be performed based on such filtered result of the template-matching procedure, but it could also be performed based on the set of deflections produced by the template-matching procedure.

The method ends in step 280, where the processor determines the value of AF complexity as a ratio between the number of far-field deflections and the number of intrinsic deflections:

$$AF\ complexity = \frac{N_F}{N_I} = \frac{N_D - N_I}{N_I} = \frac{N_D}{N_I} - 1$$

Alternatively to the implementation of step 270 described above, the process of intrinsic deflection maximum likelihood assignment may be used, as described below, to determine the number of intrinsic deflections and the number of far-field deflections.

Again, based on the candidate deflections identified in any one of the two manners described above (i.e., either obtained directly as a result of the template-matching procedure of step 250 or obtained by filtering the result of the template-matching procedure of step 250), in step 260, the processor 110 selects a subset of strong intrinsic deflections by implementing the filtering procedure described in FIG. 8. In addition, the processor 110 deploys an algorithm of intrinsic deflection maximum likelihood assignment comprising probability density estimation of the true intrinsic deflection interval distribution to assign each original candidate deflection to either a set of intrinsic deflections or a set of far-field deflections. The goal of the assignment procedure is choose a subset of the candidate deflections whose intervals maximize the relative likelihood of the estimated probability density function.

Given a probability density estimate $\Theta$ and the set of candidate deflections X, the assignment problem can be formulated as $$\max_x \left\{ \frac{L(G \mid \Delta(x))}{|x|-1} \;\middle|\; x \subseteq X \right\},$$

where $\Delta(x)$ is the set of intervals that results from the set of intrinsic deflections x and $L(\Theta|\Delta(x))$ is the likelihood of the probability density estimate $\Theta$ given the intervals that are defined by the set of deflections x.

The processor 110 may employ a greedy algorithm that starts from the set of all candidate deflections and finds a solution to the assignment problem in the following way:

1. Compute all intervals created by the current set of intrinsic deflections x
2. Sort the intervals in ascending order
3. Determine the two deflections ($x_i$ and $x_{i+1}$) that are responsible for the shortest interval
4. Determine which deflection elimination from x ($x_i$ or $x_{i+1}$) results in the largest increase of the likelihood
5. If a positive increase is found, remove the corresponding deflection from the set of deflections x and go to (1)
6. If no positive increase can be found, continue with the next shortest interval in the list and go to (3).

Figure 10:
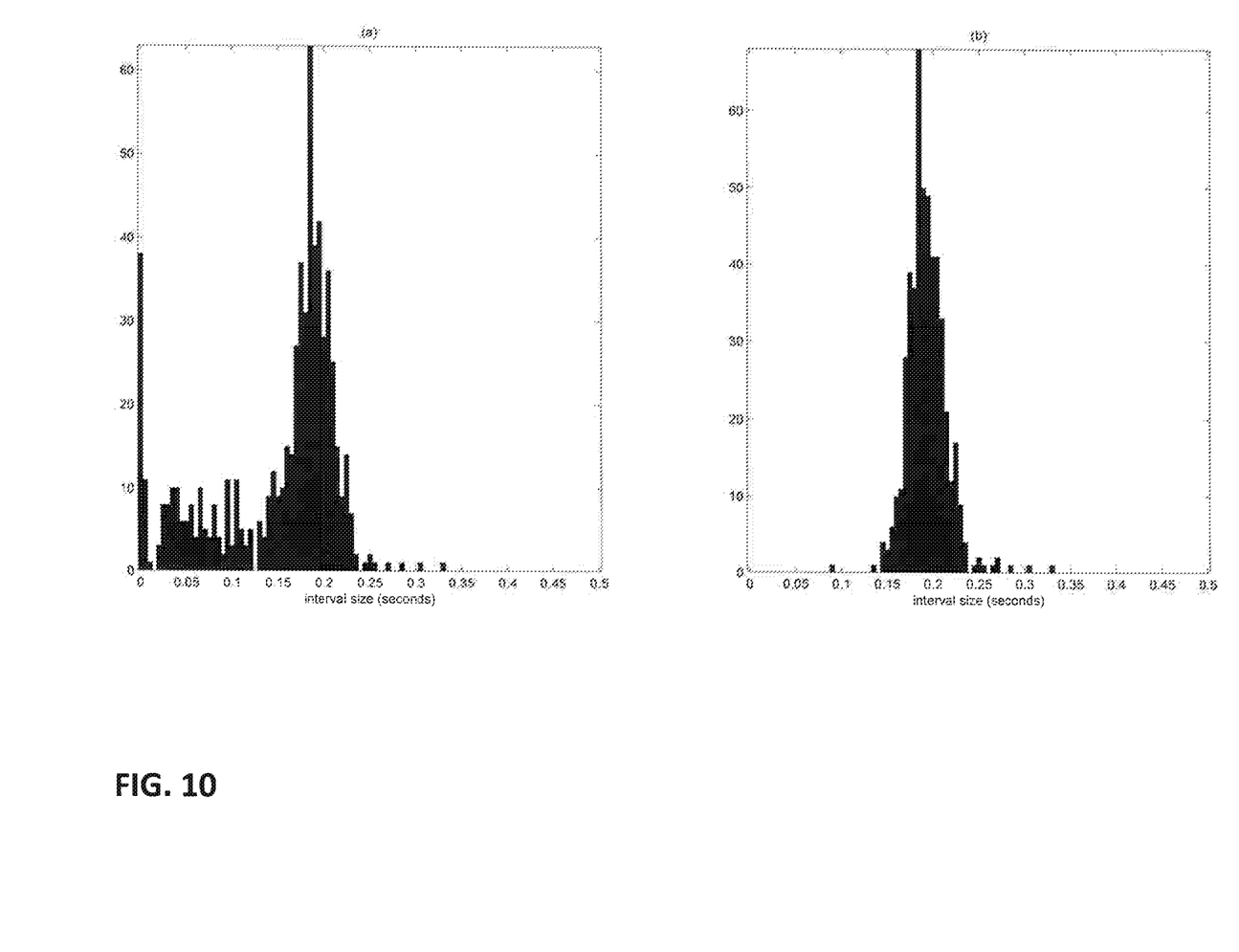
FIG. 10(a) illustrates an exemplary histogram of deflection intervals where the deflections have been filtered to remove deflections attributed to disturbances.
FIG. 10(b) illustrates an exemplary histogram of intrinsic deflection intervals after applying the greedy algorithm.

The greedy algorithm terminates when removing a deflection can no longer increase the likelihood. The solution of the deflection assignment problem is separation of the set of all deflections X into a set of intrinsic deflections I and a complementary set of far-field deflections F. An example result is shown in FIG. 10 providing graphs (a) and (b). The graph (a) depicts a histogram of deflection intervals associated with candidate deflections, where the candidate deflections were obtained by filtering the result of the template-matching procedure of step 250 with maximum interval threshold of 250 ms and a dynamic threshold for amplitude and an associated long interval percentage of 0%. The graph (b) depicts a histogram of deflection intervals after applying the greedy algorithm. Similar to the fitted Gaussian function illustrated in FIG. 9(c), the histogram of FIG. 10(b) allows estimating the value of the AFCL (as the interval corresponding to the peak of the histogram) as well as probability distribution of AFCL. For the histogram depicted in FIG. 10(b), the AFCL can be estimated to be approximately 0.2 seconds.

In step 270, the processor 110 may then use the result of the intrinsic deflection maximum likelihood assignment to compute the expected total number of true intrinsic deflections $N_I$ and the number of far-field deflections $N_F$. The number of true intrinsic deflections $N_I$ can be determined by counting the number of deflections that were assigned to the set of intrinsic deflections. The number of far-field deflections $N_F$ can be determined by counting the number of deflections that were assigned to the set of far-field deflections.

The AF complexity obtained in step 280 results in a complexity value in the range $[0, \infty]$, a low value indicating lower complexity. The value of AF complexity determined in this manner allows subsequent classification of AF and/or assignment of appropriate treatment, which could be done either by the processor 110 or by the user. Treatment may be assigned based on the classification of AF or based directly on the obtained value of AF complexity.

In case it is the processor 110 that provides a classification of AF based on the determined AF complexity value, then, in various embodiments, the processor 110 may use the AF complexity value to classify AF based on the criteria predetermined and stored in the memory 120 or based on the criteria provided by the user via the user interface 140. For example, in one embodiment, the criteria for classifying AF and assigning treatment could be such that AF complexity values in the range between 0 and 1.5 would correspond to stage I of AF and to treatment I (e.g. rhythm control), while AF complexity values greater than 1.5 would correspond to stage II of AF and to treatment II (e.g., rate control). Of course, in other embodiments, other classification schemes and other treatment assignment schemes may be used.

In various embodiments, the processor 110 may instruct display of the determined AF complexity value, the classification of AF, and/or the assigned treatment on the display 130.

Figure 11:
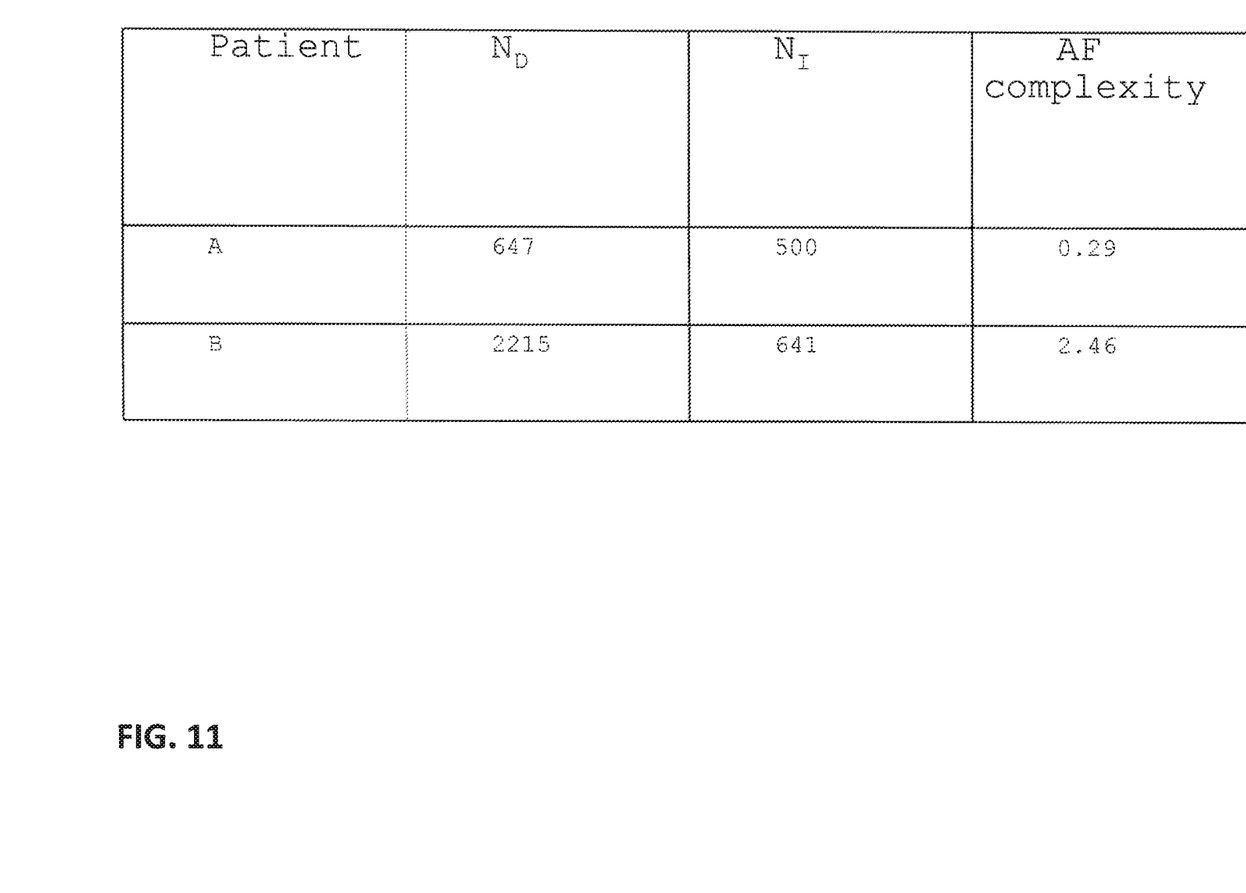
FIG. 11 illustrates the AF complexity quantification of two exemplary patients, according to one embodiment of the present invention.

When a patient with AF is referred to the emergency department, it is always difficult for the treating cardiologist to determine to what degree an AF substrate is present. Providing a tool to immediately determine the AF complexity helps the cardiologist to decide between different treatment options. FIG. 11 illustrates the AF complexity quantification of two exemplary patients, patient A and patient B. In FIG. 11, the first column is used to indicate the patient, the second column provides the total number of candidate deflections, the third column provides the number of identified strong intrinsic deflections, and the fourth column provides the determined AF complexity value.

In FIG. 11, patient A is an example of simple, non-complex AF, while patient B is an example of very complex AF. From a medical point of view, the cardiologist should attempt to cardiovert every patient to sinus rhythm by means of antiarrhythmic drugs or electrical cardioversion (rhythm control). However, if the cardiologist knows at the time of admission that patient B has very complex AF substrate (i.e. a high AF complexity value), he may choose to treat this patient by prescribing drugs that lower heart rate and prevent clotting (rate control). In other words, in the case of patient B, the presence of a complex AF may be accepted rather than initiating treatment with a low success rate, thereby avoiding side effects. In the case of patient A, rhythm control would probably be very successful. Moreover, taking into account the low AF complexity value, it could even be considered to treat patient A directly with catheter ablation as presence of AF substrate is absent or very low.

The non-invasive determination of AF complexity value in the manner described above enables a patient-tailored, individualized therapy of AF which is based on the relative degree of the complexity of AF (graded therapy). Consequently, the present invention also provides the multiple advantages of a graded AF therapy such as e.g. an increase in the success rate of rhythm control therapy and a restriction of potentially harmful interventions to patients likely responding to the therapy. In addition, comparisons of the AF complexity values determined at different points in time on the same patient and/or on different patients may be used in understanding drug effects on the fibrillatory process, thereby facilitating the development of new antiarrhythmic drugs. Longitudinal monitoring of the AF complexity may allow for studying organ-protective upstream therapy. Real-time monitoring of the AF complexity may help understanding mechanisms for cardioversion.

Various embodiments of the present invention may be built in the form of software tools using an appropriate programming language, such as e.g. MATLAB™, C#/C++/C or Java.

One embodiment of the invention may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. The computer program may be run on the processor 110.

The invention claimed is:

1. A method for determining an atrial fibrillation (AF) complexity value, comprising:
    applying a template matching algorithm to an electrocardiogram (ECG) signal to obtain a set of candidate deflections;
    identifying intrinsic deflections within the set of candidate deflections;
    based on the identified intrinsic deflections, determining a number of the intrinsic deflections and a number of far-field deflections within the set of candidate deflections; and
    determining AF complexity value as a ratio of the number of far-field deflections and the number of intrinsic deflections.

2. The method according to claim 1, wherein determining the number of intrinsic deflections and the number of far-field deflections comprises:
    determining the number of intrinsic deflections as the number of identified intrinsic deflections, and
    determining the number of far-field deflections as the difference between the total number of deflections within the set of candidate deflections and the number of identified intrinsic deflections.

3. The method according to claim 1, wherein determining the number of intrinsic deflections and the number of far-field deflections comprises:
    based on the identified intrinsic deflections, determining probability distribution of an intrinsic deflection interval,
    based on the probability distribution of the intrinsic deflection interval, assigning each deflection in the set of candidate deflections either to a set of intrinsic deflections or a set of far-field deflections,
    determining the number of intrinsic deflections as the number of deflections within the set of intrinsic deflections, and
    determining the number of far-field deflections as the number of deflections within the set of far-field deflections.

4. The method according to claim 3, wherein, the each deflection in the set of candidate deflections is assigned either to the set of intrinsic deflections or the set of far-field deflections so that a probability of the intrinsic deflection interval is maximized.

5. The method according to claim 3, wherein assigning each deflection in the set of candidate deflections either to the set of intrinsic deflections or the set of far-field deflections is performed using a greedy algorithm.

6. The method according to claim 1, wherein the intrinsic deflections are identified based on a maximum interval threshold, an order of deflection features, and a threshold for each of the deflection features.

7. The method according to claim 6, wherein the deflection features comprise one or more of a correlation coefficient of a deflection, an amplitude of the deflection, a duration of the deflection, and a slope of the deflection.

8. The method according to claim 6, wherein the threshold for each of the deflection features comprises a fixed threshold.

9. The method according to claim 6, wherein the threshold for each of the deflection features comprises a dynamic threshold and the intrinsic deflections are identified further based on a percentage of intervals that are allowed to exceed the maximum interval threshold.

10. The method according to claim 1, further comprising classifying the AF based on the determined AF complexity value.

11. The method according to claim 1, further comprising selecting a treatment from a set of treatments based on the determined AF complexity value.

12. The method according to claim 1, further comprising determining AF cycle length based on the identified intrinsic deflections.

13. The method according to claim 1, wherein the ECG signal comprises a trans-esophageal ECG signal.

14. An electrocardiogram (ECG) device comprising:
    a processor configured to apply a template matching algorithm to an electrocardiogram (ECG) signal to obtain a set of candidate deflections, identify intrinsic deflections within the set of candidate deflections, based on the identified intrinsic deflections, determine a number of the intrinsic deflections and a number of far-field deflections within the set of candidate deflection, and determine AF complexity value as a ratio of the number of far-field deflections and the number of intrinsic deflections; and
    a device operably coupled to the processor configured to display the determined AF complexity value.

15. The electrocardiogram device according to claim 14, wherein the processor is configured to:
    determine the number of intrinsic deflections as the number of identified intrinsic deflections, and
    determine the number of far-field deflections as the difference between the total number of deflections within the set of candidate deflections and the number of identified intrinsic deflections.

16. The electrocardiogram device according to claim 14, wherein the processor is configured to:
    based on the identified intrinsic deflections, determine probability distribution of an intrinsic deflection interval,
    based on the probability distribution of the intrinsic deflection interval, assign each deflection in the set of candidate deflections either to a set of intrinsic deflections or a set of far-field deflections,
    determine the number of intrinsic deflections as the number of deflections within the set of intrinsic deflections, and
    determine the number of far-field deflections as the number of deflections within the set of far-field deflections.

17. The electrocardiogram device according to claim 14, wherein the processor is configured to classify the AF based on the determined AF complexity value.

18. The electrocardiogram device according to claim 14, wherein the processor is configured to determine AF cycle length based on the identified intrinsic deflections.

19. The electrocardiogram device according to claim 14, wherein the ECG signal comprises a trans-esophageal ECG signal.

20. A computer readable storage medium having instructions configured for, when executed by a processor, performing a method comprising:
- applying a template matching algorithm to an electrocardiogram (ECG) signal to obtain a set of candidate deflections;
- identifying intrinsic deflections within the set of candidate deflections,
- based on the identified intrinsic deflections, determining a number of the intrinsic deflections and a number of far-field deflections within set of candidate deflections; and
- determining AF complexity value as a ratio of the number of far-field deflections and the number of intrinsic deflections.

* * * * *